US00PP34969P3

(12) United States Plant Patent
Warrington

(10) Patent No.: US PP34,969 P3
(45) Date of Patent: Feb. 7, 2023

(54) ***GERANIUM* PLANT NAMED 'STORM CLOUD'**

(50) Latin Name: ***Geranium pratense* (L.)**
Varietal Denomination: Storm Cloud

(71) Applicant: Helen Warrington, Llanybrydder (GB)

(72) Inventor: Helen Warrington, Llanybrydder (GB)

( * ) Notice: Subject to any disclaimer, the term of this patent is extended or adjusted under 35 U.S.C. 154(b) by 0 days.

(21) Appl. No.: 17/742,811

(22) Filed: May 12, 2022

(65) Prior Publication Data

US 2022/0369527 P1 Nov. 17, 2022

(30) Foreign Application Priority Data

May 14, 2021 (QZ) ..... 20211282

(51) Int. Cl.
*A01H 5/02* (2018.01)
*A01H 6/42* (2018.01)

(52) U.S. Cl.
USPC ..... Plt./324
CPC ..... *A01H 6/42* (2018.05); *A01H 6/425* (2018.05)

(58) Field of Classification Search
USPC ..... Plt./324
CPC ..... A01H 5/02
See application file for complete search history.

(56) References Cited

PUBLICATIONS

CPVO Register Consultation 4.1.67 Citation for'Storm Cloud'; Jun. 3, 2022; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Geranium* plant named 'Storm Cloud' that is distinguishable by palmate, deeply cleaved foliage which is dark green in color together with red-purple margins which extend into the leaves. 'Storm Cloud' bears single and semi-double flowers which are dark blue in color and which contain red-purple stamens and modified petaloid stamens appearing as a red-purple "eye" within the flower.

2 Drawing Sheets

Genus and species: *Geranium pratense* (L.).
Variety denomination: 'Storm Cloud'.

CROSS-REFERENCE TO RELATED APPLICATION

This patent application claims the benefit of priority from Community Plant Variety Rights Application No. 20211282 as filed on May 14, 2021, the contents of which is incorporated herein by reference for all it teaches and discloses.

BACKGROUND OF THE NEW PLANT

The present invention comprises a new and distinct variety of *Geranium*, botanically known as *Geranium pratense* (L.) and hereinafter referred to by the variety name 'Storm Cloud'. 'Storm Cloud' originated from an open pollination in 2015 in Ty-Cwm, Wales, Great Britain from a group of *Geranium* plants named 'Victor Reiter' Group. The inventor believes that California nurseryman Victor Reiter bred and introduced *Geranium* 'Victor Reiter' (unpatented) as a dark-leafed *Geranium pratense* in the 1970s. Seeds and seed-raised plants from 'Victor Reiter' are widely circulated in commerce, with some variations. It is common for nurserymen to offer the variety as *Geranium* 'Victor Reiter', or *Geranium* 'Victor Reiter' Group, or *Geranium* 'Victor Reiter' Strain. The inventor selected 'Storm Cloud' as a single seedling raised from seed collected from plants in production at the inventor's nursery, acquired as *Geranium* 'Victor Reiter' Group'. The female parent of 'Storm Cloud' is an unnamed seed-raised derivative of *Geranium* 'Victor Reiter'.

A seedling was selected in 2015 and subsequently named 'Storm Cloud'. 'Storm Cloud' was first vegetatively propagated by division in Ty-Cwm, Wales. 'Storm Cloud' was found to reproduce true to type in successive generations of asexual propagation via tissue culture in Ty-Cwm, Wales.

SUMMARY

The following are the most outstanding and distinguishing characteristics of this new variety when grown under normal horticultural practices in Ty-Cwm, Wales.

1. The foliage of 'Storm Cloud' is palmate and deeply cleaved.
2. The foliage of 'Storm Cloud' is dark green in color, with red-purple margins which extend into the leaves.
3. 'Storm Cloud' bears single and semi-double flowers.
4. The flowers of 'Storm Cloud' are dark blue in color.
5. The semi-double flowers of 'Storm Cloud' bear smaller inner petals and modified petaloid stamens.
6. The stamens and modified petaloid stamens of 'Storm Cloud' are red-purple in color, appearing as a red-purple "eye" within the flower.

DESCRIPTION OF THE PHOTOGRAPH

Figure 1:
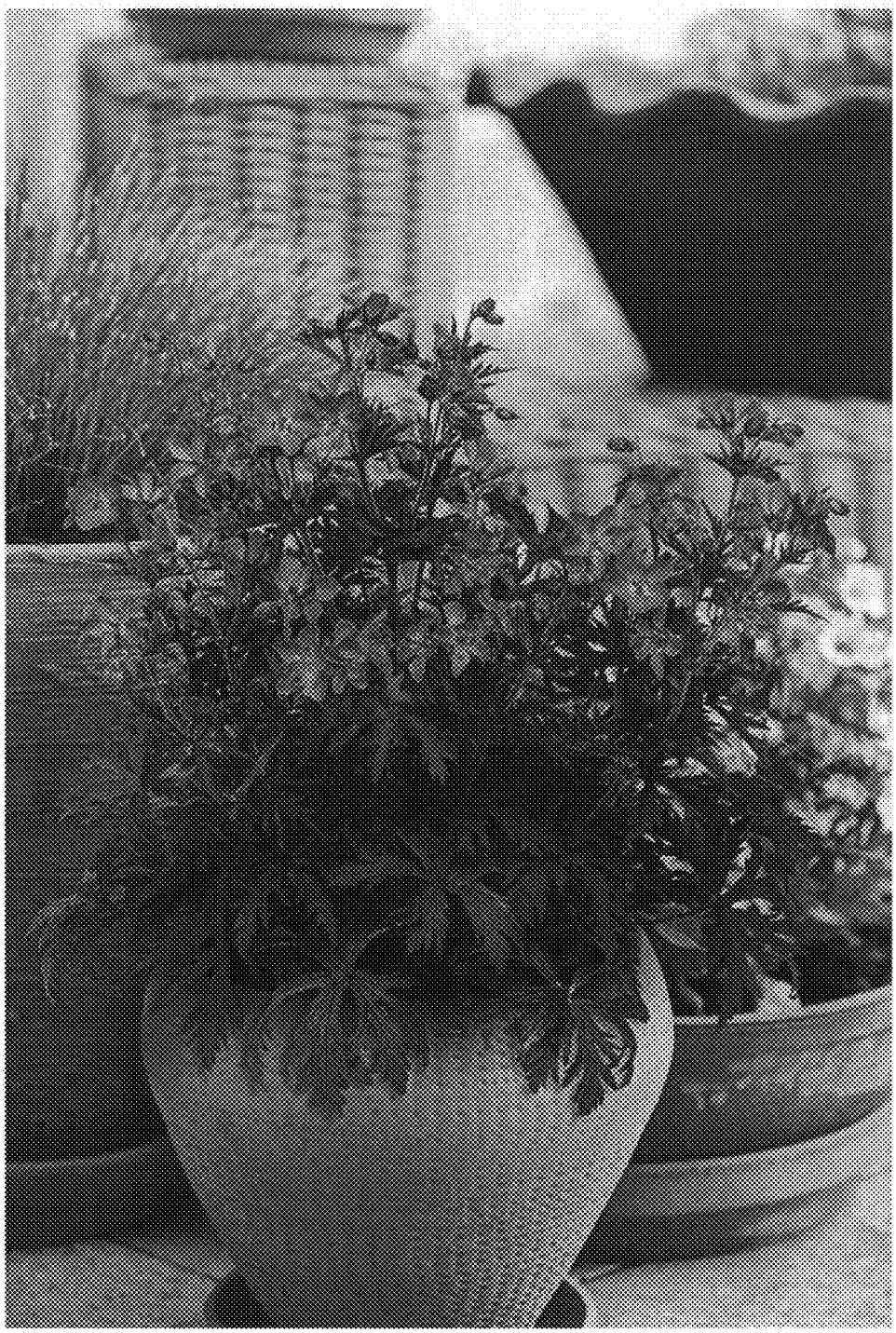
Figure 2:
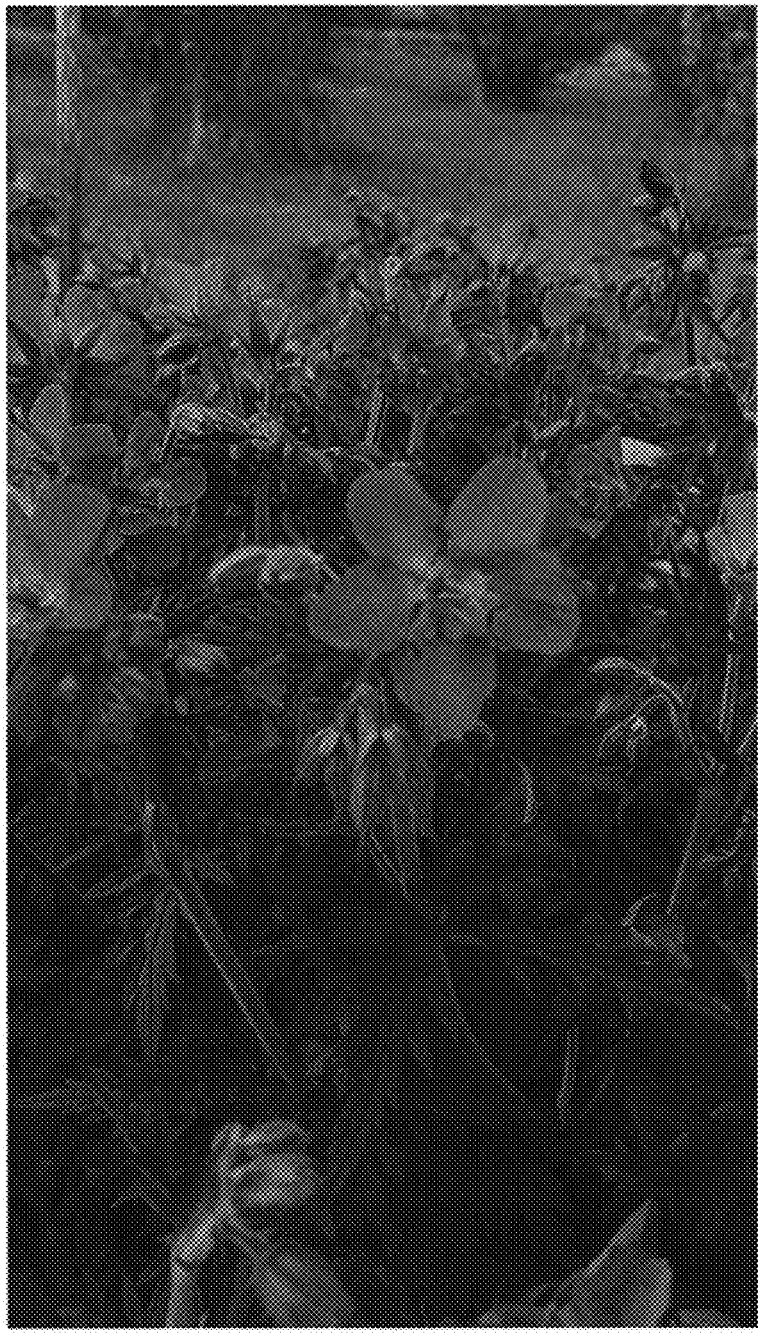

This new *Geranium* plant is illustrated by the accompanying photographs which shows:

FIG. 1 shows a fifteen months old plant of 'Storm Cloud' grown in a pot; and FIG. 2 shows a close-up view of the flowers of 'Storm Cloud'.

The colors shown are as true as can be reasonably obtained by conventional photographic procedures.

DESCRIPTION OF THE NEW VARIETY

The following detailed descriptions set forth the distinctive characteristics of 'Storm Cloud'. Observations, measurements, values, and comparisons were collected in July 2022 in Santa Barbara, Calif. from a fifteen months old plant which was growing outdoors in full sun in a 3 gallon container in Santa Barbara, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Geraniaceae.

*Botanical*.—*Geranium pratense* (L.).

*Common name*.—*Geranium*.

*Designation*.—'Storm Cloud'.

Parentage:

*Female parent*.—Unnamed seed-raised derivative of *Geranium* 'Victor Reiter'.

*Male parent*.—Unnamed seed-raised derivative of *Geranium* 'Victor Reiter'.

Plant:

*Propagation method*.—Division or tissue culture.

*Rooting system*.—Slightly fleshy, developing fibrous root branches and fine root hairs. Root color 199D, root hair color NN155C.

*Vigor*.—Moderate vigor.

*Time to develop roots*.—2-3 weeks to develop roots on a division or for a tissue culture explant to become viable on its own roots.

*Recommended rooting temperature*.—20° C.-22° C.

*Crop time*.—Approximately 15 months are required to produce a budded and flowering plant in a 1 gallon container. Larger containers require a longer period of growth in order to fill out.

*Natural flowering season*.—Continually from May to September.

*Suggested container size*.—1-gallon container.

*Use*.—Ornamental for use as a landscape plant or container plant.

*Type*.—Perennial.

*Form*.—Upright, vase-shaped becoming spreading when mature in the landscape.

*Height* (*from top of soil*).—First year: 35.0 cm. Mature: 60.0 cm.

*Width* (*horizontal plant diameter*).—First year: 30.0 cm. Mature: 40.0 cm.

*Cultural requirements*.—Grow in full sun with moderate water and well-draining soil.

*Hardiness*.—Hardy to −20° C.

Stems, branches:

*Description*.—All primary stems are basal, arising at or from below ground level. Basal stems bear secondary or lateral branches at each node.

*Quantity*.—Approximately 40, of which 12-15 are primary basal stems and 25-30 are secondary branches.

*Shape*.—Terete.

*Length*.—8 cm to 10 cm measured to base of inflorescence.

*Diameter*.—3.5 mm at base, 2 mm at base of inflorescence.

*Aspect*.—The primary basal stems are upward growing; the secondary or lateral branches emerge and grow upward at approximately 30° away from the primary stems.

*Internode length* (*primary and secondary stems*).—Varies between 2 cm and 4 cm.

*Stem and branch color*.—Initial growth and in full shade: Green 145A-145B. Stems exposed to sun rapidly develop anthocyanin pigmentation, color 184A.

*Stem surface*.—Puberulent.

*Stem strength*.—Semi-stiff, wiry.

Leaves:

*Shape*.—Orbicular overall, palmate, deeply cleft into 6-8 lobes, each lobe itself cleft into 5-7 secondary lobes.

*Arrangement*.—Opposite.

*Attachment*.—Sessile.

*Aspect*.—Slightly raised above horizontal

*Quantity per branch*.—6-10 (3-5 opposite pairs).

*Dimensions overall*.—11 cm in diameter.

*Dimensions of each lobe*.—5.5 cm in length, 3 cm in width.

*Dimensions of each secondary lobe*.—0.5-1.5 cm in length, 0.3-0.6 cm in width.

*Margin overall and lobes*.—Smooth.

*Venation*.—Pinnate.

*Veins*.—Adaxial surface: depressed, color as leaf. Abaxial surface: raised, color as leaf.

*Texture* (*both surfaces*).—Slightly rough, glabrous, matte.

*Color*.—Adaxial surface: N189A. Abaxial surface: N138C. Margins, including lobe margins: 187A extending inwards up to 1 mm into adaxial surface.

*Apex* (*including all lobes*).—Acute.

*Base*.—Truncate. Lobes basally fused.

*Fragrance*.—Very slight, grass-like.

Peduncle:

*Length*.—8 mm-12 mm.

*Shape*.—Terete.

*Diameter*.—1.5 mm.

*Color*.—184A.

*Texture*.—Puberulent, very fine short hairs, color as peduncle, 184A.

Inflorescence:

*Type*.—Terminal raceme. Flowers arranged in opposite pairs.

*Length*.—8 cm to 10 cm.

*Width*.—5 cm.

Pedicel:

*Length*.—6 mm-12 mm.

*Diameter*.—1.0-1.5 mm.

*Color*.—184A.

*Texture*.—Puberulent, very fine short hairs, color as peduncle, 184A.

Stipules: Present in opposite pairs at base of pedicel.

*Shape*.—Lanceolate.

*Dimensions*.—7 mm in length, 3 mm in width.

*Color* (*both surfaces*).—61B.

*Texture*.—Smooth, glabrous, margins entire.

Calyx:

*Shape*.—Campanulate.

*Dimensions*.—5 mm in height, 22 mm in diameter (across sepal apices).

Sepals:

*Quantity, arrangement*.—5, free.

*Length*.—9 mm.

*Width*.—4 mm when flattened.

*Shape*.—Boat shaped, adaxial surface concave.

*Apex*.—Acuminate with single fine hair extending 2 mm-3 mm, hair color 187A.

*Base*.—Truncate.

*Margin*.—Entire.

*Color*.—Adaxial surface: 147B. Abaxial surface: 189A with 3-5 parallel longitudinal veins, color 187A.

*Texture*.—Adaxial surface: Glabrous, glossy. Abaxial surface: Glabrous, matte.

Flowers:

*Type*.—Cyme

*Quantity*.—Up to 30 buds and flowers per branch, and approximately 400-500 buds and flowers per plant, of which approximately one-fifth are open at any one time.

*Shape*.—Rotate, single and semi-double.

*Dimensions*.—3.5 cm-4.0 cm in diameter. Single flowers consist of 5 free petals. Semi-double flowers consist of one whorl of 5 free outer petals and 3-5 free inner smaller petals or petaloid stamens.

*Lastingness of blooms*.—Petals not persistent. Each flower lasts for approximately 5 days.

*Fragrance*.—None.

Bud (immediately prior to petal emergence):

*Shape*.—Ellipsoidal, apex shallow acute, base rounded.

*Dimensions*.—8 mm in length, 6 mm in diameter.

*Surface*.—Ribbed (5 longitudinal ribs), puberulent, very short fine hairs, color 187A. Strongly pubescent, especially apex. Hairs dense, fine, 1 mm in length, color 71A.

*Color*.—189A with 3-5 parallel longitudinal veins, color 187A.

Petals (single flowers):

*Quantity*.—5.

*Arrangement*.—Rotate, free and overlapping when opening, non-overlapping when flower fully expanded.

*Shape*.—Broadly ovate.

*Petal dimensions*.—18 mm-20 mm in length, 14 mm-15 mm in width.

*Apex*.—Rounded.

*Base*.—Cuneate.

*Margin*.—Smooth, entire.

*Surfaces* (*both*).—Smooth, glabrous, semi-glossy.

*Petal color* (*both surfaces*).—At first opening, 101A; when fully expanded, 104C.

*Petal base and veins*.—Color very pale blue, almost white, nearest to N155A.

Petals (semi-double flowers):

*Description*.—Semi-double flowers consist of one whorl of outer petals as in single flowers, and one inner whorl of irregularly shaped smaller petals or a combination of smaller petals and modified (petaloid) stamens.

*Inner petals or petaloid stamens*.—Quantity: 5, varying from 1 petal and 4 petaloid stamens to 5 petaloid stamens. Arrangement: Rotate, free, petals (where present) overlapping. Shape: Irregular, obovate to spatulate. Dimensions: 6 mm-10 mm in length, 2 mm-7 mm in width. Margin: Smooth, entire. Surfaces (both): Smooth, glabrous, semi-glossy. Petal color (inner petals, both surfaces): 104C with occasional streaks 71B. Petaloid stamen color: Predominantly 71B.

Reproductive organs:

*Stamens*.—Quantity: 10 including up to 5 modified (petaloid) stamens. Filament (true stamens) dimensions: 2 mm-4 mm in length, 1.5 mm in diameter. Filament color: 70D-71D. Anthers: Shape, dimensions: ellipsoid, 2.5 mm in length, 1.5 mm in width. Anther color: 151C. Pollen: None observed.

*Pistil*.—Quantity: 1. Style dimensions: 3 mm in length, 1.5 mm in diameter. Style color: 70D. Stigma: botanically 5, but appear as one roughly circular mass. Color: 144B.

*Ovary* (*only observed unfertilized*).—Shape: Ovoid, length 1.5 mm, diameter 1 mm. Color: 150B.

Seed: None observed.

Pest and disease resistance and susceptibility: Resistant to slugs and rabbits, susceptible to aphids (*aphis gossypii*) when stressed. Less susceptible to powdery mildew (*Erysiphacea* spp.) that affects perennial *Geraniums* generally.

Drought tolerance: Drought tolerant.

COMPARISON WITH FEMALE PARENT VARIETY

'Storm Cloud' can be compared to the female parent commercial variety. Differences between the two varieties are described in Table 1:

TABLE 1

Comparison with Female Parent Variety

| Characteristic | 'Storm Cloud' | Female Parent |
|---|---|---|
| Size | Taller and wider than the Female Parent | Shorter and narrower than 'Storm Cloud' |
| Flower color | Darker and more intense blue than the Female Parent | Lighter and less intense than 'Storm Cloud' |

COMPARISON WITH CLOSE VARIETY

All commercial varieties of *Geranium pratense* known to the inventor only bear single flowers with the exception of *Geranium pratense* 'Summer Skies' (U.S. Plant Pat. No. 10,695.) Whereas the flowers of 'Storm Cloud' are dark blue and semi-double in form, the flowers of 'Summer Skies' are pale violet-blue and single and more fully double in form.

I claim:

1. A new and distinct cultivar of *Geranium* Plant Named 'Storm Cloud' as described and illustrated herein.

* * * * *